United States Patent
Hook et al.

(10) Patent No.: US 9,896,704 B2
(45) Date of Patent: Feb. 20, 2018

(54) **METHOD FOR PRODUCING L-ISOLEUCINE USING A BACTERIUM OF THE FAMILY *ENTEROBACTERIACEAE* HAVING OVEREXPRESSED THE CYCA GENE**

(71) Applicant: AJINOMOTO CO., INC., Tokyo (JP)

(72) Inventors: Christina Dmitrievna Hook, Moscow (RU); Valery Vasilievich Samsonov, Moscow (RU); Natalia Sergeevna Eremina, Moscow (RU); Natalia Viktorovna Stoynova, Moscow (RU); Tatiyana Sergeevna Sidorova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/097,632

(22) Filed: Apr. 13, 2016

(65) Prior Publication Data

US 2016/0312254 A1    Oct. 27, 2016

(30) Foreign Application Priority Data

Apr. 22, 2015    (RU) ................................ 2015114955

(51) Int. Cl.
*C12P 13/06* (2006.01)
*C07K 14/245* (2006.01)

(52) U.S. Cl.
CPC ............ *C12P 13/06* (2013.01); *C07K 14/245* (2013.01)

(58) Field of Classification Search
None
See application file for complete search history.

(56) References Cited

U.S. PATENT DOCUMENTS

| | | | |
|---|---|---|---|
| 3,058,888 A | 10/1962 | Chibata et al. | |
| 3,231,478 A | 1/1966 | Uemura et al. | |
| 3,262,861 A | 7/1966 | Kinoshita et al. | |
| 3,767,529 A | 10/1973 | Yoshinaga et al. | |
| 4,278,765 A | 7/1981 | Debabov et al. | |
| 4,346,170 A | 8/1982 | Sano et al. | |
| 4,601,983 A | 7/1986 | Nakamori et al. | |
| 4,656,135 A | 4/1987 | Tsuchida et al. | |
| 5,362,637 A | 11/1994 | Kino et al. | |
| 5,661,012 A | 8/1997 | Sano et al. | |
| 5,830,716 A | 11/1998 | Kojima et al. | |
| 5,965,391 A | 10/1999 | Reinscheid et al. | |
| 5,998,178 A | 12/1999 | Hashiguchi et al. | |
| 6,040,160 A | 3/2000 | Kojima et al. | |
| 8,460,903 B2 | 6/2013 | Savrasova et al. | |
| 8,673,597 B2 | 3/2014 | Wakasa et al. | |
| 8,679,798 B2 | 3/2014 | Yampolskaya et al. | |
| 8,852,897 B2 | 10/2014 | Savrasova et al. | |
| 9,029,104 B2 | 5/2015 | Samsonova et al. | |
| 9,175,319 B2 | 11/2015 | Stoynova et al. | |
| 2002/0110876 A1 | 8/2002 | Miyata et al. | |
| 2005/0170474 A1 | 8/2005 | Yamamoto et al. | |
| 2006/0216796 A1 | 9/2006 | Hashiguchi et al. | |
| 2011/0281311 A1 | 11/2011 | Wakasa et al. | |
| 2012/0237986 A1 | 9/2012 | Ziyatdinov et al. | |
| 2014/0335574 A1 | 11/2014 | Sycheva et al. | |
| 2015/0017693 A1 | 1/2015 | Sycheva et al. | |
| 2016/0312254 A1* | 10/2016 | Hook ...................... C12P 13/06 |

FOREIGN PATENT DOCUMENTS

| | | |
|---|---|---|
| EP | 0685555 | 12/1995 |
| EP | 1179597 | 2/2002 |
| EP | 1484410 | 12/2004 |
| EP | 2360263 | 8/2011 |
| JP | 60-12995 | 1/1985 |
| JP | 61-15696 | 1/1986 |
| JP | 02-000458 | 1/1990 |
| JP | 05-130882 | 5/1993 |
| WO | WO95/11985 | 5/1995 |
| WO | WO95/16042 | 6/1995 |
| WO | WO96/15246 | 5/1996 |

OTHER PUBLICATIONS

Schneider et al., (Appl. Microbio Biotech, 2004, vol. 65, pp. 576-582).*
Schneider, F., et al., "Identification and characterization of the main β-alanine uptake system in *Escherichia coli*," Appl. Microbiol. Biotechnol. 2004;65:576-582.
Extended European Search Report for European Patent App. No. 16166148.3 (dated Sep. 13, 2016).
Jojima, T., et al., "Amino Acids, Branched Chain, L-Isoleucine," Encyclopedia of Industrial Biotechnology: Bioprocess, Bioseparation, and Cell Technology, 2010, pp. 1-6.
Komatsubara, "Amino acids: Genetically Engineered S. marcescens," Recombinant Microbes for Industrial and Agricultural Applications, 1994, pp. 474 and 477.
Terasawa, M., et al., "Depression of by-product formation during L-isoleucine production by a living-cell reaction process," Appl. Microbial. Biotechnol. 1991;35:348-351.
Terasawa, et al., "Industrial Production by Native Immobilization," Industrial Application of Immobilized Biocatalysts, 1993, pp. 44-52.

* cited by examiner

*Primary Examiner* — Hope Robinson
(74) *Attorney, Agent, or Firm* — Cermak Nakajima & McGowan LLP; Shelly Guest Cermak

(57) ABSTRACT

The present invention provides a method for producing L-isoleucine by fermentation using a bacterium belonging to the family Enterobacteriaceae which has been modified to overexpress the cycA gene. The method also allows reducing the amount of byproduct amino acids that are produced during fementative production of L-isoleucine using Enterobacteriaceae bacterium having an L-isoleucine-producing ability.

4 Claims, No Drawings

SEQUENCE LISTING

```
<160> NUMBER OF SEQ ID NOS: 13

<210> SEQ ID NO 1
<211> LENGTH: 1413
<212> TYPE: DNA
<213> ORGANISM: Escherichia coli

<400> SEQUENCE: 1
atggtagatc aggtaaaagt cgttgccgat gatcaggctc cggctgaaca gtcgctacgg      60
cgcaatctca caaaccgaca tattcagctt attgccattg gcggtgccat tggtacgggg     120
ttgtttatgg ggtctggcaa aacgattagc cttgccgggc cgtcgatcat tttcgtttat     180
atgatcattg gttttatgct cttttttcgtg atgcgggcaa tgggggaatt gctgctttcg     240
aatctggaat acaaatcttt tagtgacttc gcttccgatt tactcgggcc gtgggcagga     300
tatttcaccg gctggactta ctggttctgc tgggttgtaa ccggtatggc agacgtggtg     360
```

```
gcgatcacgg cttatgctca gttctggttc cccgatctct ccgactgggt cgcctcgctg    420
gcggtgatag tgctgctgct gacgctcaat ctcgccaccg tgaaaatgtt cggtgagatg    480
gagttctggt ttgcgatgat caaaatcgtc gccattgtgt cgctgattgt cgtcggcctg    540
gtcatggtgg cgatgcactt tcagtcaccg actggtgtgg aagcgtcatt cgcgcatttg    600
tggaatgacg gcggctggtt cccgaaaggt ttaagtggct tctttgccgg attccagata    660
gcggttttcg ctttcgtggg gattgagctg gtaggtacaa cagctgcgga aaccaaagat    720
ccagagaaat cactgccacg cgcgattaac tccattccga tccgtatcat tatgttctac    780
gtcttcgcgc tgattgtgat tatgtccgtg acgccgtgga gttcggtagt cccggagaaa    840
agcccgtttg ttgaactgtt cgtgttggta gggctgcctg ctgccgcaag cgtgatcaac    900
tttgtggtgc tgacctctgc ggcgtcttcc gctaacagcg gcgtcttctc taccagccgt    960
atgctgtttg gtctggcgca ggaaggtgtg gcaccgaaag cgttcgctaa actttctaag    1020
cgcgcagtac ccgcgaaagg gctgacgttc tcgtgtatct gtctgctcgg cggcgtggtg    1080
atgttgtatg tgaatcctag tgtgattggc gcgttcacga tgattacaac cgtttccgcg    1140
attctgttta tgttcgtctg gacgattatc ctttgctcgt accttgtgta tcgcaaacag    1200
cgtcctcatc tacatgagaa gtcgatctac aagatgccgc tcggcaagct gatgtgctgg    1260
gtatgtatgg cgttctttgt gttcgtggtc gtgttgctga cactggaaga tgacactcgc    1320
caggcgctgc tggttacccc gctgtggttt atcgcgctgg ggttgggctg gctgtttatt    1380
ggtaagaagc gggctgctga actgcggaaa taa                                 1413
```

<210> SEQ ID NO 2
<211> LENGTH: 470
<212> TYPE: PRT
<213> ORGANISM: Escherichia coli

<400> SEQUENCE: 2

```
Met Val Asp Gln Val Lys Val Val Ala Asp Asp Gln Ala Pro Ala Glu
1               5                   10                  15

Gln Ser Leu Arg Arg Asn Leu Thr Asn Arg His Ile Gln Leu Ile Ala
            20                  25                  30

Ile Gly Gly Ala Ile Gly Thr Gly Leu Phe Met Gly Ser Gly Lys Thr
        35                  40                  45

Ile Ser Leu Ala Gly Pro Ser Ile Ile Phe Val Tyr Met Ile Ile Gly
    50                  55                  60

Phe Met Leu Phe Phe Val Met Arg Ala Met Gly Glu Leu Leu Leu Ser
65                  70                  75                  80

Asn Leu Glu Tyr Lys Ser Phe Ser Asp Phe Ala Ser Asp Leu Leu Gly
                85                  90                  95

Pro Trp Ala Gly Tyr Phe Thr Gly Trp Thr Tyr Trp Phe Cys Trp Val
            100                 105                 110

Val Thr Gly Met Ala Asp Val Val Ala Ile Thr Ala Tyr Ala Gln Phe
        115                 120                 125

Trp Phe Pro Asp Leu Ser Asp Trp Val Ala Ser Leu Ala Val Ile Val
    130                 135                 140

Leu Leu Leu Thr Leu Asn Leu Ala Thr Val Lys Met Phe Gly Glu Met
145                 150                 155                 160

Glu Phe Trp Phe Ala Met Ile Lys Ile Val Ala Ile Val Ser Leu Ile
                165                 170                 175

Val Val Gly Leu Val Met Val Ala Met His Phe Gln Ser Pro Thr Gly
```

```
            180                 185                 190
Val Glu Ala Ser Phe Ala His Leu Trp Asn Asp Gly Gly Trp Phe Pro
            195                 200                 205
Lys Gly Leu Ser Gly Phe Phe Ala Gly Phe Gln Ile Ala Val Phe Ala
            210                 215                 220
Phe Val Gly Ile Glu Leu Val Gly Thr Thr Ala Ala Glu Thr Lys Asp
225                 230                 235                 240
Pro Glu Lys Ser Leu Pro Arg Ala Ile Asn Ser Ile Pro Ile Arg Ile
            245                 250                 255
Ile Met Phe Tyr Val Phe Ala Leu Ile Val Ile Met Ser Val Thr Pro
            260                 265                 270
Trp Ser Ser Val Val Pro Glu Lys Ser Pro Phe Val Glu Leu Phe Val
            275                 280                 285
Leu Val Gly Leu Pro Ala Ala Ser Val Ile Asn Phe Val Val Leu
            290                 295                 300
Thr Ser Ala Ala Ser Ser Ala Asn Ser Gly Val Phe Ser Thr Ser Arg
305                 310                 315                 320
Met Leu Phe Gly Leu Ala Gln Glu Gly Val Ala Pro Lys Ala Phe Ala
            325                 330                 335
Lys Leu Ser Lys Arg Ala Val Pro Ala Lys Gly Leu Thr Phe Ser Cys
            340                 345                 350
Ile Cys Leu Leu Gly Gly Val Val Met Leu Tyr Val Asn Pro Ser Val
            355                 360                 365
Ile Gly Ala Phe Thr Met Ile Thr Thr Val Ser Ala Ile Leu Phe Met
            370                 375                 380
Phe Val Trp Thr Ile Ile Leu Cys Ser Tyr Leu Val Tyr Arg Lys Gln
385                 390                 395                 400
Arg Pro His Leu His Glu Lys Ser Ile Tyr Lys Met Pro Leu Gly Lys
            405                 410                 415
Leu Met Cys Trp Val Cys Met Ala Phe Phe Val Phe Val Val Leu
            420                 425                 430
Leu Thr Leu Glu Asp Asp Thr Arg Gln Ala Leu Leu Val Thr Pro Leu
            435                 440                 445
Trp Phe Ile Ala Leu Gly Leu Gly Trp Leu Phe Ile Gly Lys Lys Arg
            450                 455                 460
Ala Ala Glu Leu Arg Lys
465                 470

<210> SEQ ID NO 3
<211> LENGTH: 64
<212> TYPE: DNA
<213> ORGANISM: Artificial
<220> FEATURE:
<223> OTHER INFORMATION: Primer P1

<400> SEQUENCE: 3
cccgtaagcg tgtattttg tgagctgttt cgcgttcgct caagttagta taaaaagct      60 gaac                                                                 64

<210> SEQ ID NO 4
<211> LENGTH: 65
<212> TYPE: DNA
<213> ORGANISM: Artificial
<220> FEATURE:
<223> OTHER INFORMATION: Primer P2

<400> SEQUENCE: 4
```

```
gatcatcggc aacgactttt acctgatcta ccatgtttag ttctccttcc ggccaatgct    60
tcgtt                                                                65

<210> SEQ ID NO 5
<211> LENGTH: 1964
<212> TYPE: DNA
<213> ORGANISM: Artificial
<220> FEATURE:
<223> OTHER INFORMATION: DNA-fragment 1

<400> SEQUENCE: 5
cccgtaagcg tgtatttttg tgagctgttt cgcgttcgct caagttagta taaaaaagct    60
gaacgagaaa cgtaaaatga tataaatatc aatatattaa attagatttt gcataaaaaa   120
cagactacat aatactgtaa aacacaacat atgcagtcac tatgaatcaa ctacttagat   180
ggtattagtg acctgtaaca gactgcagtg gtcgaaaaaa aaagcccgca ctgtcaggtg   240
cgggcttttt tctgtgttaa gcttcgacga atttctgcca ttcatccgct tattatcact   300
tattcaggcg tagcaccagg cgtttaaggg caccaataac tgccttaaaa aaattacgcc   360
ccgccctgcc actcatcgca gtactgttgt aattcattaa gcattctgcc gacatggaag   420
ccatcacaga cggcatgatg aacctgaatc gccagcggca tcagcacctt gtcgccttgc   480
gtataatatt tgcccatggt gaaaacgggg gcgaagaagt tgtccatatt ggccacgttt   540
aaatcaaaac tggtgaaact cacccaggga ttggctgaga cgaaaaacat attctcaata   600
aaccctttag ggaaataggc caggttttca ccgtaacacg ccacatcttg cgaatatatg   660
tgtagaaact gccggaaatc gtcgtggtat tcactccaga gcgatgaaaa cgtttcagtt   720
tgctcatgga aaacggtgta acaagggtga acactatccc atatcaccag ctcaccgtct   780
ttcattgcca tacggaattc cggatgagca ttcatcaggc gggcaagaat gtgaataaag   840
gccggataaa acttgtgctt atttttcttt acggtcttta aaaaggccgt aatatccagc   900
tgaacggtct ggttataggt acattgagca actgactgaa atgcctcaaa atgttcttta   960
cgatgccatt gggatatatc aacggtggta tatccagtga ttttttttctc cattttagct  1020 tccttagctc ctgaaaatct cggatccgat atctagctag agcgcccggt tgacgctgct  1080
agtgttacct agcgatttgt atcttactgc atgttacttc atgttgtcaa tacctgtttt  1140
tcgtgcgact tatcaggctg tctacttatc cggagatcca caggacgggt gtggtcgcca  1200
tgatcgcgta gtcgatagtg gctccaagta gcgaagcgag caggactggg cggcggccaa  1260
agcggtcgga cagtgctccg agaacgggtg cgcatagaaa ttgcatcaac gcatatagcg  1320
ctagcagcac gccatagtga ctggcgatgc tgtcggaatg gacgatatcc cgcaagaggc  1380
ccggcagtac cggcataacc aagcctatgc ctacagcatc cagggtgacg gtgccgagga  1440
tgacgatgag cgcattgtta gatttcatac acggtgcctg actgcgttag caatttaact  1500
gtgataaact accgcattaa agcttatcga tgataagctg tcaaacatga gaattcgaaa  1560
tcaaataatg attttatttt gactgatagt gacctgttcg ttgcaacaaa ttgataagca  1620 atgcttttttt ataatgccaa cttagtataa aaaagcaggc ttcaagatct tcacctacca  1680
aacaatgccc cctgcaaaaa ataaattca tataaaaaac atacagataa ccatctgcgg  1740
tgataaatta tctctggcgg tgttgacata ataccactg gcggtgatac tgagcacatc  1800
agcaggacgc actgaccacc atgaaggtga cgctcttaaa aattaagccc tgaagaaggg  1860
cagcattcaa agcagaaggc tttggggtgt gtgatacgaa acgaagcatt ggccggaagg  1920
```
agaactaaac atggtagatc aggtaaaagt cgttgccgat gatc            1964

<210> SEQ ID NO 6
<211> LENGTH: 20
<212> TYPE: DNA
<213> ORGANISM: Artificial
<220> FEATURE:
<223> OTHER INFORMATION: Primer P3

<400> SEQUENCE: 6
gttcagcacc ctggtgtttg            20

<210> SEQ ID NO 7
<211> LENGTH: 20
<212> TYPE: DNA
<213> ORGANISM: Artificial
<220> FEATURE:
<223> OTHER INFORMATION: Primer P4

<400> SEQUENCE: 7
cgccaatggc aataagctga            20

<210> SEQ ID NO 8
<211> LENGTH: 457
<212> TYPE: DNA
<213> ORGANISM: Artificial
<220> FEATURE:
<223> OTHER INFORMATION: DNA-fragment 2

<400> SEQUENCE: 8
gttcagcacc ctggtgtttg aagtcgaact gctggaaatc ctctaagcag cgcattctgt   60
tcccctcgaa cgagagggga gcaggcattc agcaataaac ccttcagttt gccaaacggc  120
gctattttgt gttgcaaaga ccccgtaagc gtgtattttt gtgagctgtt tcgcgttatc  180
accgtgatat gacactcact ttaaacataa attaacatt agatctaaat cttagtattc  240
atcccgcgta ttgttaccta atatcgatga gtcccgatac agattcgtcg tatcatagac  300
tgactaaagg ccgtagagcc tgaacaacac agacaggtac aggaagaaaa aaacatggta  360
gatcaggtaa aagtcgttgc cgatgatcag gctccggctg aacagtcgct acggcgcaat  420
ctcacaaacc gacatattca gcttattgcc attggcg                           457

<210> SEQ ID NO 9
<211> LENGTH: 2174
<212> TYPE: DNA
<213> ORGANISM: Artificial
<220> FEATURE:
<223> OTHER INFORMATION: DNA-fragment 3

<400> SEQUENCE: 9
gttcagcacc ctggtgtttg aagtcgaact gctggaaatc ctctaagcag cgcattctgt   60
tcccctcgaa cgagagggga gcaggcattc agcaataaac ccttcagttt gccaaacggc  120
gctattttgt gttgcaaaga ccccgtaagc gtgtattttt gtgagctgtt tcgcgttcgc  180
tcaagttagt ataaaaaagc tgaacgagaa acgtaaaatg atataaatat caatatatta  240
aattagattt tgcataaaaa acagactaca taatactgta aaacacaaca tatgcagtca  300
ctatgaatca actacttaga tggtattagt gacctgtaac agactgcagt ggtcgaaaaa  360
aaaagcccgc actgtcaggt gcgggcttttt ttctgtgtta gcttcgacg aatttctgcc  420 attcatccgc ttattatcac ttattcaggc gtagcaccag gcgttaagg gcaccaataa  480 ctgccttaaa aaattacgc cccgccctgc cactcatcgc agtactgttg taattcatta  540

```
agcattctgc cgacatggaa gccatcacag acggcatgat gaacctgaat cgccagcggc    600
atcagcacct tgtcgccttg cgtataatat ttgcccatgg tgaaaacggg ggcgaagaag    660
ttgtccatat tggccacgtt taaatcaaaa ctggtgaaac tcacccaggg attggctgag    720
acgaaaaaca tattctcaat aaacccttta gggaaatagg ccaggttttc accgtaacac    780
gccacatctt gcgaatatat gtgtagaaac tgccggaaat cgtcgtggta ttcactccag    840
agcgatgaaa acgtttcagt ttgctcatgg aaaacggtgt aacaagggtg aacactatcc    900
catatcacca gctcaccgtc tttcattgcc atacggaatt ccggatgagc attcatcagg    960
cgggcaagaa tgtgaataaa ggccggataa aacttgtgct tattttttctt tacggtctttt   1020 aaaaaggccg taatatccag ctgaacggtc tggttatagg tacattgagc aactgactga   1080
aatgcctcaa aatgttcttt acgatgccat tgggatatat caacggtggt atatccagtg   1140
atttttttct ccattttagc ttccttagct cctgaaaatc tcggatccga tatctagcta   1200
gagcgcccgg ttgacgctgc tagtgttacc tagcgatttg tatcttactg catgttactt   1260
catgttgtca ataccgtttt ttcgtgcgac ttatcaggct gtctacttat ccggagatcc   1320
acaggacggg tgtggtcgcc atgatcgcgt agtcgatagt ggctccaagt agcgaagcga   1380
gcaggactgg gcggcggcca aagcggtcgg acagtgctcc gagaacgggt gcgcatagaa   1440
attgcatcaa cgcatatagc gctagcagca cgccatagtg actggcgatg ctgtcggaat   1500
ggacgatatc ccgcaagagg cccggcagta ccggcataac caagcctatg cctacagcat   1560
ccagggtgac ggtgccgagg atgacgatga gcgcattgtt agatttcata cacggtgcct   1620
gactgcgtta gcaatttaac tgtgataaac taccgcatta aagcttatcg atgataagct   1680
gtcaaacatg agaattcgaa atcaaataat gatttattt tgactgatag tgacctgttc   1740
gttgcaacaa attgataagc aatgcttttt tataatgcca acttagtata aaaaagcagg   1800
cttcaagatc ttcacctacc aaacaatgcc cccctgcaaa aataaattc atataaaaaa    1860 catacagata accatctgcg gtgataaatt atctctggcg gtgttgacat aaataccact   1920
ggcggtgata ctgagcacat cagcaggacg cactgaccac catgaaggtg acgctcttaa   1980
aaattaagcc ctgaagaagg gcagcattca agcagaaggc tttggggtg tgtgatacga    2040 aacgaagcat tggccggaag gagaactaaa catggtagat caggtaaaag tcgttgccga   2100
tgatcaggct ccggctgaac agtcgctacg gcgcaatctc acaaaccgac atattcagct   2160
tattgccatt ggcg                                                     2174
```

<210> SEQ ID NO 10
<211> LENGTH: 28
<212> TYPE: DNA
<213> ORGANISM: Artificial
<220> FEATURE:
<223> OTHER INFORMATION: Primer P5

<400> SEQUENCE: 10

```
cgctcaagtt agtataaaaa agctgaac                                        28
```

<210> SEQ ID NO 11
<211> LENGTH: 28
<212> TYPE: DNA
<213> ORGANISM: Artificial
<220> FEATURE:
<223> OTHER INFORMATION: Primer P6

<400> SEQUENCE: 11

```
tgaagcctgc tttttatac taagttgg                                          28

<210> SEQ ID NO 12
<211> LENGTH: 1541
<212> TYPE: DNA
<213> ORGANISM: Artificial
<220> FEATURE:
<223> OTHER INFORMATION: DNA-fragment 4

<400> SEQUENCE: 12
cgctcaagtt agtataaaaa agctgaacga gaaacgtaaa atgatataaa tatcaatata      60
ttaaattaga ttttgcataa aaaacagact acataatact gtaaaacaca acatatgcag    120
tcactatgaa tcaactactt agatggtatt agtgacctgt aacagactgc aggggggggg    180
gggaaagcca cgttgtgtct caaaatctct gatgttacat tgcacaagat aaaaatatat    240
catcatgaac aataaaactg tctgcttaca taaacagtaa tacaaggggt gttatgagcc    300
atattcaacg ggaaacgtct tgctcgaggc cgcgattaaa ttccaacatg gatgctgatt    360
tatatgggta taaatgggct cgcgataatg tcgggcaatc aggtgcgaca atctatcgat    420
tgtatgggaa gcccgatgcg ccagagttgt ttctgaaaca tggcaaaggt agcgttgcca    480
atgatgttac agatgagatg gtcagactaa actggctgac ggaatttatg cctcttccga    540
ccatcaagca ttttatccgt actcctgatg atgcatggtt actcaccact gcgatccccg    600
ggaaaacagc attccaggta ttagaagaat atcctgattc aggtgaaaat attgttgatg    660
cgctggcagt gttcctgcgc cggttgcatt cgattcctgt ttgtaattgt ccttttaaca    720
gcgatcgcgt atttcgtctc gctcaggcgc aatcacgaat gaataacggt ttggttgatg    780
cgagtgattt tgatgacgag cgtaatggct ggcctgttga acaagtctgg aaagaaatgc    840
ataagctttt gccattctca ccggattcag tcgtcactca tggtgatttc tcacttgata    900
accttatttt tgacgagggg aaattaatag gttgtattga tgttggacga gtcggaatcg    960
cagaccgata ccaggatctt gccatcctat ggaactgcct cggtgagttt ctccttcat   1020 tacagaaacg ctttttcaa aaatatggta ttgataatcc tgatatgaat aaattgcagt   1080
ttcatttgat gctcgatgag ttttttctaat cagaattggt taattggttg taacactggc   1140
agagcattac gctgacttga cgggacggcg ctttgttga ataaatcgaa cttttgctga   1200
gttgaaggat cagatcacgc atcttcccga caacgcagac cgttccgtgg caaagcaaaa   1260
gttcaaaatc accaactggt ccacctacaa caaagctctc atcaaccgtg gctccctcac   1320
tttctggctg gatgatgggg cgattcaggc ctggtatgag tcagcaacac cttcttcacg   1380
aggcagacct cagcgccccc ccccccctgc aggtcgacgg atccggggaa ttcgaaatca   1440
aataatgatt ttattttgac tgatagtgac ctgttcgttg caacaaattg ataagcaatg   1500
cttttttata atgccaactt agtataaaaa agcaggcttc a                       1541

<210> SEQ ID NO 13
<211> LENGTH: 2087
<212> TYPE: DNA
<213> ORGANISM: Artificial
<220> FEATURE:
<223> OTHER INFORMATION: DNA-fragment 5

<400> SEQUENCE: 13
gttcagcacc ctggtgtttg aagtcgaact gctggaaatc tctaagcag cgcattctgt       60 tccctcgaa cgagagggga gcaggcattc agcaataaac ccttcagttt gccaaacggc    120
gctattttgt gttgcaaaga ccccgtaagc gtgtattttt gtgagctgtt tcgcgtttga    180
```

-continued

```
agcctgcttt tttatactaa gttggcatta taaaaaagca ttgcttatca atttgttgca    240
acgaacaggt cactatcagt caaaataaaa tcattatttg atttcgaatt ccccggatcc    300
gtcgacctgc aggggggggg gggcgctgag gtctgcctcg tgaagaaggt gttgctgact    360
cataccaggc ctgaatcgcc ccatcatcca gccagaaagt gagggagcca cggttgatga    420
gagctttgtt gtaggtggac cagttggtga ttttgaactt ttgctttgcc acggaacggt    480
ctgcgttgtc gggaagatgc gtgatctgat ccttcaactc agcaaaagtt cgatttattc    540
aacaaagccg ccgtcccgtc aagtcagcgt aatgctctgc cagtgttaca accaattaac    600
caattctgat tagaaaaact catcgagcat caaatgaaac tgcaatttat tcatatcagg    660
attatcaata ccatattttt gaaaaagccg tttctgtaat gaaggagaaa actcaccgag    720
gcagttccat aggatggcaa gatcctggta tcggtctgcg attccgactc gtccaacatc    780
aatacaacct attaatttcc cctcgtcaaa aataaggtta tcaagtgaga aatcaccatg    840
agtgacgact gaatccggtg agaatggcaa aagcttatgc atttctttcc agacttgttc    900
aacaggccag ccattacgct cgtcatcaaa atcactcgca tcaaccaaac cgttattcat    960
tcgtgattgc gcctgagcga gacgaaatac gcgatcgctg ttaaaaggac aattacaaac   1020
aggaatcgaa tgcaaccggc gcaggaacac tgccagcgca tcaacaatat tttcacctga   1080
atcaggatat tcttctaata cctggaatgc tgttttcccg gggatcgcag tggtgagtaa   1140
ccatgcatca tcaggagtac ggataaaatg cttgatggtc ggaagaggca taaattccgt   1200
cagccagttt agtctgacca tctcatctgt aacatcattg gcaacgctac ctttgccatg   1260
tttcagaaac aactctggcg catcgggctt cccatacaat cgatagattg tcgcacctga   1320
ttgcccgaca ttatcgcgag cccatttata cccatataaa tcagcatcca tgttggaatt   1380
taatcgcggc ctcgagcaag acgtttcccg ttgaatatgg ctcataacac cccttgtatt   1440
actgtttatg taagcagaca gttttattgt tcatgatgat atattttttat cttgtgcaat   1500 gtaacatcag agattttgag acacaacgtg gctttccccc cccccctgc agtctgttac    1560 aggtcactaa taccatctaa gtagttgatt catagtgact gcatatgttg tgttttacag   1620
tattatgtag tctgtttttt atgcaaaatc taatttaata tattgatatt tatatcattt   1680
tacgtttctc gttcagcttt tttatactaa cttgagcgag atcttcacct accaaacaat   1740 gccccccctgc aaaaaataaa ttcatataaa aaacatacag ataaccatct gcggtgataa   1800
attatctctg gcggtgttga cataaatacc actggcggtg atactgagca catcagcagg   1860
acgcactgac caccatgaag gtgacgctct taaaaattaa gccctgaaga agggcagcat   1920
tcaaagcaga aggctttggg gtgtgtgata cgaaacgaag cattggccgg aaggagaact   1980
aaacatggta gatcaggtaa aagtcgttgc cgatgatcag gctccggctg aacagtcgct   2040
acggcgcaat ctcacaaacc gacatattca gcttattgcc attggcg                  2087
```

METHOD FOR PRODUCING L-ISOLEUCINE USING A BACTERIUM OF THE FAMILY *ENTEROBACTERIACEAE* HAVING OVEREXPRESSED THE CYCA GENE

This application claims priority under 35 U.S.C. § 119 to Russian Patent Application No. 2015114955, filed Apr. 22, 2015, the entirety of which is incorporated by reference herein. Also, the Sequence Listing filed electronically herewith is hereby incorporated by reference (File name: 2016-04-13T_US-543_Seq_List; File size: 18 KB; Date recorded: Apr. 13, 2016).

BACKGROUND OF THE INVENTION

Field of the Invention

The present invention relates generally to the microbiological industry, and specifically to a method for producing L-isoleucine by fermentation of a bacterium of the family Enterobacteriaceae which has been modified to overexpress the cycA gene, so that production of byproduct amino acid(s) of L-isoleucine is reduced.

Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acids production yields have been reported, including transformation of microorganisms with recombinant DNA (see, for example, U.S. Pat. No. 4,278,765 A) and alteration of expression regulatory regions such as promoters, leader sequences, and/or attenuators, or others known to the person skilled in the art (see, for example, US20060216796 A1 and WO9615246 A1). Other techniques for enhancing production yields include increasing the activities of enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, and phosphate fluxes, and genes encoding toxins, etc.

L-isoleucine is an essential amino acid in humans and other animals, and it can be used as a material for various medicinal drugs. For example, L-isoleucine can be used as a nutritional supplement to promote nutrition. L-isoleucine has two chiral centers in its carbon backbone, one of which is its central (alpha) carbon atom and the other is its beta carbon atom in the side chain. It is therefore difficult to industrially synthesize the L-isomer; that is, the 2S,3S-isomer of isoleucine by a chemical synthetic method with a high grade of purity at a low price.

L-isoleucine can be produced from its various precursors, such as, for example, alpha-aminobutyric acid ($\alpha$ABA), alpha-hydroxybutyric acid ($\alpha$HBA), threonine, aspartic acid, or fumaric acid, when a microorganism is cultured in a medium containing the precursor, a carbon source, a nitrogen source, and other nutrients (U.S. Pat. Nos. 3,058,888, 3,262,861, and 3,231,478).

A method for producing L-isoleucine by native immobilization of cells of the *Brevibacterium flavum* strain AB-07 that can metabolize precursors in biosynthetic pathways of L-isoleucine, such as alpha-aminobutyric acid ($\alpha$ABA) and alpha-ketobutyric acid ($\alpha$KBA), has been developed (Terasawa M. et al., Depression of by-product formation during L-isoleucine production by a living-cell reaction process, Appl. Microbiol. Biotechnol., 1991, 35(3):348-351). Furthermore, the living cell reaction (LCR) process was applied to the immobilized cells of the *Corynebacterium glutamicum* (formerly *Brevibacterium flavum*) strain MJ-233 to produce L-isoleucine from ethanol as the energy source and $\alpha$KBA as the precursor (overviewed in Jojima, T., Inui, M. and Yukawa, H. Amino acids, branched chain, L-isoleucine// Encyclopedia of industrial biotechnology: bioprocess, bioseparation, and cell technology, pp. 1-6, M. C. Flickinger (ed.), John Wiley & Sons, Inc., 2010). However, these methods require the use of expensive precursors and, therefore, are not considered useful for industrial production of L-isoleucine at a low price.

Furthermore, methods for producing L-isoleucine have been disclosed which include a method utilizing *Escherichia coli* (*E. coli*) resistant to isoleucine analogs (Japanese Patent Laid-open Publication No. 5-130882), a method utilizing a recombinant strain of *E. coli* integrated with a DNA-fragment encoding threonine deaminase (Japanese Patent Laid-open Publication No. 2-458), a method utilizing the mutant microorganisms belonging to the genus *Corynebacterium* resistant to methyllysine (Japanese Patent Laid-open Publication No. 61-15696) or amino-hydroxyvaleric acid (AHVA) (U.S. Pat. No. 3,767,529), and a method utilizing a recombinant strain of *Corynebacterium glutamicum* transformed with a gene encoding homoserine dehydrogenase (Japanese Patent Laid-open Publication No. 60-12995). It is also known that L-isoleucine-producing ability can be imparted by introducing the thrABC operon containing the thrA gene encoding aspartate kinase I/homoserine dehydrogenase I derived from *E. coli*, of which inhibition by L-threonine is substantially desensitized, and the ilvGMEDA operon containing the ilvA gene encoding threonine deaminase, of which inhibition by L-isoleucine is substantially desensitized and from which a region required for attenuation is removed (EP0685555 B1).

It has also been reported that the ability to produce substances such as L-amino acids can be improved by increasing enzymatic activity of nicotinamide nucleotide transhydrogenase (also referred to as "transhydrogenase") in microbial cells, so that the producing ability of the microorganism for reduced nicotinamide adenine dinucleotide phosphate (NADPH) is increased (WO9511985 A1). In this reference, an example of improvement of L-isoleucine-producing ability of *E. coli* by the increase of the transhydrogenase activity is also mentioned. A further method for producing L-isoleucine discloses the use of a bacterium belonging to the genus *Escherichia* that has been modified to enhance the intracellular phosphoenolpyruvate carboxylase and transhydrogenase activities (EP1179597 B1).

However, a well-known disadvantage of L-isoleucine production by fermentation of a microorganism is the accumulation of byproduct amino acids in a relatively large amount as compared with the amount of the L-isoleucine that is produced (Terasawa M. et al., 1991; Komatsubara, S. Amino acids: genetically engineered *Serratia marcescens*/ Recombinant microbes for industrial and agricultural applications, pp. 474-477, Y. Murooka and T. Imanaka (eds.), Marcel Dekker, Inc., 1994; Terasawa, M. and Yukawa, H. Industrial production of biochemicals by native immobilization//Industrial application of immobilized biocatalysts, pp. 44-52, A. Tanaka, T. Tosa and T. Kobayashi (eds.), Marcel Dekker, Inc., 1993; Jojima T. et al., 2010). Byproduct amino acids, such as, for example, valine (Val), leucine (Leu), alanine (Ala), glycine (Gly), norvaline (nVal), O-ethyl-homoserine (O-EH) and alpha-aminobutyric acid (αABA), can accumulate considerably in fermentation liqueur during fermentation of L-isoleucine-producing microorganisms. Because the physicochemical characteristics of the byproduct amino acids produced during L-isoleucine fermentation are very similar to those of L-isoleucine, it is very difficult to isolate L-isoleucine with a sufficient grade of purity at a reasonable price using ordinary separation methods such as, for example, chromatography. It is therefore of particular importance to reduce the production of byproduct amino acids in the method for producing L-isoleucine by fermentation. From the viewpoint of industrial production, the improvement of a method for producing L-isoleucine by fermentation of L-isoleucine-producing microorganisms that are devoid of or produce less byproduct amino acids represents a great challenge since such an improved method has the potential to produce L-isoleucine with the high grade of purity at a low price.

A method for reducing production of byproducts of a target substance by deleting or attenuating the biosynthesis system of the byproduct has been reported (for example, "Amino acid fermentation" Gakkai Shuppan Center, p. 4, 1986). However, in this method, when a microorganism is cultured, the aforementioned byproduct needs to be added to the medium in the amount necessary for growth of the microorganism. Further methods for reducing production of byproduct amino acids, such as L-tryptophan, L-phenylalanine, L-isoleucine and/or L-valine (EP1484410 A1) or L-glutamic acid (EP 2360263 A1), by enhancing a system for cell uptake of the byproduct of a target substance have been also disclosed. For example, the cell system for L-leucine uptake (LivK) was enhanced in *E. coli* to reduce by-production of L-leucine when the bacterium was cultivated to produce L-isoleucine as the target substance (EP1484410 A1).

However, no data has been previously reported that demonstrates the effect of overexpression of the cycA gene on production of L-isoleucine and byproduct amino acids by fermentation of an L-isoleucine-producing bacterium of the family Enterobacteriaceae.

SUMMARY OF THE INVENTION

An improved method of producing L-isoleucine by fermentation of a bacterium of the family Enterobacteriaceae is described herein. According to the presently disclosed subject matter, production of L-isoleucine by fermentation of a bacterium of the family Enterobacteriaceae can be increased. Specifically, production of L-isoleucine by fermentation of a bacterium of the family Enterobacteriaceae can be improved by overexpressing the cycA gene in the bacterium, so that the production of L-isoleucine by the modified bacterium can be increased. Increase of L-isoleucine production can be an absolute amount, or a relative amount to the byproduct amino acid(s). Furthermore, when L-isoleucine is produced by fermentation of a bacterium of the family Enterobacteriaceae, production of byproduct amino acids can be reduced. Specifically, the method for producing L-isoleucine by fermentation of a bacterium of the family Enterobacteriaceae can be improved by overexpressing the cycA gene in the bacterium, so that the production of byproduct amino acid(s) such as L-leucine, L-valine, L-norleucine, L-norvaline and alpha-aminobutyric acid by the modified bacterium can be reduced. Reduction of byproduct amino acid production can be an absolute amount of byproduct amino acid(s), or relative to the amount of L-isoleucine produced. Therefore, in an embodiment, a larger amount of L-isoleucine with respect to the byproduct amino acid(s) can be produced, and as a result of simplifying the purification process of the L-isoleucine produced by the method described herein, the produced L-isoleucine is at a high grade of purity and is produced at a low price.

It is one aspect of the present invention to provide a method for producing L-isoleucine comprising:

(i) cultivating a bacterium of the family Enterobacteriaceae which has an ability to produce L-isoleucine in a culture medium to produce the L-isoleucine in the culture medium or the bacterial cells, or both; and (ii) collecting the L-isoleucine from the culture medium or the bacterial cells, or both, wherein the bacterium has been modified to overexpress the cycA gene.

It is a further aspect of the present invention to provide the method as described above, wherein the cycA gene encodes a protein selected from the group consisting of:

(A) a protein comprising the amino acid sequence of SEQ ID NO: 2;

(B) a protein comprising the amino acid sequence of SEQ ID NO: 2, but which includes one or more mutations comprising substitution, deletion, insertion and/or addition of one or several amino acid residues, and wherein said protein has the activity of a transporter having the amino acid sequence of SEQ ID NO: 2; and (C) a protein having a homology of not less than 70% with respect to the entire amino acid sequence of SEQ ID NO: 2 and having the activity of the transporter having the amino acid sequence of SEQ ID NO: 2.

It is a further aspect of the present invention to provide the method as described above, wherein the cycA gene is a DNA selected from the group consisting of:

(A) a DNA comprising the nucleotide sequence of SEQ ID NO: 1;

(B) a DNA encoding a protein comprising the amino acid sequence of SEQ ID NO: 2, but which includes one or more mutations comprising substitution, deletion, insertion and/or addition of one or several amino acid residues, and wherein said protein has the activity of the transporter having the amino acid sequence of SEQ ID NO: 2; and (C) a DNA which is a variant nucleotide sequence of SEQ ID NO: 1 due to the degeneracy of the genetic code.

It is a further aspect of the present invention to provide the method as described above, wherein the cycA gene is overexpressed by increasing the copy number of the cycA gene and/or by modifying an expression regulatory region of the cycA gene, so that the expression of the gene is enhanced as compared with a non-modified bacterium.

It is a further aspect of the present invention to provide the method as described above, wherein the bacterium belongs to the genus *Escherichia*.

It is a further aspect of the present invention to provide the method as described above, wherein the bacterium is *Escherichia coli*.

It is a further aspect of the present invention to provide the method as described above, wherein the bacterium belongs to the genus *Pantoea*.

It is a further aspect of the present invention to provide the method as described above, wherein the bacterium is *Pantoea ananatis*.

It is a further aspect of the present invention to provide the method as described above, wherein an amount of a byproduct amino acid is reduced as compared with a non-modified bacterium.

It is a further aspect of the present invention to provide the method as described above, wherein the byproduct amino acid is selected from the group consisting of L-valine, L-leucine, L-norvaline, L-norleucine, alpha-aminobutyric acid and a combinations thereof.

DESCRIPTION OF THE PREFERRED EMBODIMENTS

The present invention is described in detail below.

1. Bacterium

Any L-isoleucine-producing bacterium belonging to the family Enterobacteriaceae and modified to overexpress the cycA gene can be used. The phrase "an L-isoleucine-producing bacterium" can mean a bacterium of the family Enterobacteriaceae which has an ability to produce, excrete or secrete, and/or cause accumulation of L-isoleucine in a culture medium and/or the bacterial cells when the bacterium is cultured in the medium.

The phrase "an L-isoleucine-producing bacterium" can also mean a bacterium which has an ability to produce, excrete or secrete, and/or cause accumulation of L-isoleucine in a culture medium in an amount larger than a wild-type or parental strain, such as E. coli K-12, and can also mean a bacterium that is able to cause accumulation in the medium of an amount, for example, not less than 0.1 g/L, not less than 0.5 g/L, or not less than 1.0 g/L of L-isoleucine.

Furthermore, the bacterium belonging to the family Enterobacteriaceae and modified to overexpress the cycA gene, which has an ability to produce L-isoleucine, can also be used. The bacterium may inherently have the ability to produce L-isoleucine or may be modified to have an ability to produce L-isoleucine by using a mutation method or DNA recombination techniques. The bacterium can be obtained by overexpressing the cycA gene in a bacterium that inherently has the ability to produce L-isoleucine, or in a bacterium that has already been imparted with the ability to produce L-isoleucine. Alternatively, the bacterium can be obtained by imparting the ability to produce L-isoleucine to a bacterium already modified to overexpress the cycA gene. Also, the bacterium can acquire the ability to produce L-isoleucine by being modified to overexpress the cycA gene.

The phrase "an ability to produce L-isoleucine" can mean the ability of a bacterium of the family Enterobacteriaceae to produce, excrete or secrete, and/or cause accumulation of L-isoleucine in a culture medium and/or the bacterial cells to such a level that the L-isoleucine can be collected from the culture medium and/or the bacterial cells when the bacterium is cultured in the medium.

The bacterium can produce L-isoleucine either alone or as a mixture of L-isoleucine and one or more kinds of amino acids that are different from L-isoleucine, such as, for example, amino acids in L-form (also referred to as L-amino acids). Furthermore, the bacterium can produce L-isoleucine either alone or as a mixture of L-isoleucine and one or more kinds of hydroxycarboxylic acids.

Furthermore, a bacterium belonging to the family Enterobacteriaceae, which has an ability to produce L-isoleucine and has been modified to overexpress the cycA gene, such that production of byproduct amino acid(s) is reduced as compared with a non-modified strain, for example, a wild-type or parental strain as described hereinafter, can be used.

Specifically, the bacterium can be used, which has been modified to overexpress the cycA gene and which is able to produce one, two, or more kinds of byproduct amino acids of L-isoleucine production at a lower level than a non-modified strain, or in which by-production of one, two, or more kinds of byproduct amino acids of L-isoleucine is reduced as compared with a non-modified strain.

The phrase "able to produce byproduct amino acids of L-isoleucine production" as used herein with regard to a bacterium can mean the ability of a bacterium of the family Enterobacteriaceae to produce, excrete or secrete, and/or cause accumulation of one, two, or more kinds of byproduct amino acids of L-isoleucine production in a culture medium or the bacterial cells, or both, to such a level that the one, two or more byproduct amino acids of L-isoleucine production can be collected from the culture medium and/or the bacterial cells when the bacterium is cultured in the medium. The phrase "a byproduct amino acid of L-isoleucine production" is explained hereinafter.

The phrase "amino acid" can mean an organic compound containing at least one amino group ($NH_2$) and at least one carboxyl group (COOH). An L-amino acid is a non-limiting example of an amino acid.

The phrase "L-amino acid" can mean L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine. Other non-limiting examples of an L-amino acid include norvaline (nVal) or L-norvaline, norleucine (nLeu) or L-norleucine, 0-ethyl-homoserine (O-EH) or O-ethyl-L-homoserine, and alpha-aminobutyric acid ($\alpha$ABA) or L-alpha-aminobutyric acid.

The phrase "amino acid" or "L-amino acid" can refer not only to an amino acid in a free form, but may also include a salt or a hydrate of the amino acid, or an adduct formed by the amino acid and another organic or inorganic compound. The phrase "amino acid" can mean, for example, sodium, potassium, ammonium, monochlorhydrate, and so forth salts of an amino acid such as, for example, monochlorhydrate salt of L-lysine (L-lysine.HCl) or monochlorhydrate salt of L-arginine (L-arginine.HCl). An example of a hydrate of an amino acid includes L-cysteine monohydrate (L-Cys×$H_2O$).

The phrase "hydroxycarboxylic acid" can mean an organic compound containing at least one hydroxyl group (OH) and at least one carboxylic group (COOH). An alpha-hydroxycarboxylic acid is an example of a hydroxycarboxylic acid. Specific and non-limiting examples of alpha-hydroxycarboxylic acids include L-lactic acid, citric acid, and L-alpha-hydroxybutyric acid ($\alpha$HBA).

The phrase "a byproduct amino acid of L-isoleucine production" can refer to one, two or more byproduct amino acids of L-isoleucine and can mean a substance, such as, for example, an organic compound, which is different from L-isoleucine and which is produced as a byproduct, co-product, or side-product during the production of L-isoleucine by fermentation of a bacterium belonging to the family Enterobacteriaceae that has an ability to produce L-isoleucine. The phrase "a byproduct amino acid of L-isoleucine production" can also refer to a substance that can be produced and excreted or secreted by a bacterium of the family Enterobacteriaceae, that has an ability to produce L-isoleucine, during fermentation of the bacterium to produce L-isoleucine, such that the substance accumulates in a culture medium or the bacterial cells, or both, to such a level that the substance can be collected from the culture medium and/or the bacterial cells when the bacterium is cultured in the medium. An amount of a byproduct amino acid of L-isoleucine production in the culture medium and/or the bacterial cells can be lower, equal or higher than the amount of L-isoleucine produced by fermentation of a bacterium belonging to the family Enterobacteriaceae that has an ability to produce L-isoleucine. However, the amount of a byproduct amino acid of L-isoleucine production in the culture medium and/or the bacterial cells is preferably lower than the amount of L-isoleucine.

Specific examples of a byproduct amino acid of L-isoleucine production include, but are not limited to, an intermediate in a biosynthetic pathway of L-isoleucine or a product of another biosynthetic pathway that branches off from the biosynthetic pathway of L-isoleucine, and so forth, or their combination. The intermediate is not limited to an intermediate in the biosynthetic pathway of L-isoleucine, and it also may be a precursor, an intermediate or a substrate in a metabolic pathway of other one, two or more substances, for example, a precursor, an intermediate or a substrate in a biosynthetic pathway of a branched-chain L-amino acid when the target substance is L-isoleucine.

The phrase "a branched-chain L-amino acid" can refer to the L-amino acids such as L-valine, L-leucine, and L-isoleucine, and may also refer to L-norvaline and L-norleucine. As pyruvic acid (may be also referred to as "alpha-ketopropionic acid") is a precursor in the biosynthetic pathway of L-isoleucine, a byproduct of L-isoleucine can be the product of another biosynthetic pathway that branches off from pyruvic acid in the biosynthetic pathway of L-isoleucine. A byproduct amino acid of L-isoleucine is a particular example of the product of another biosynthetic pathway that branches off from pyruvic acid in the biosynthetic pathway of L-isoleucine, and can include L-valine and L-leucine that have the common precursor 2-oxoisovaleric acid (may be also referred to as "alpha-ketoisovaleric acid"), L-norvaline and L-norleucine that have the common precursor 2-oxovaleric acid (may be also referred to as "alpha-ketovaleric acid"), which 2-oxoisovaleric acid and 2-oxovaleric acid have the common precursor pyruvic acid.

A non-limiting example of an intermediate in a metabolic pathway of a substance, that is different from L-isoleucine, includes alpha-aminobutyric acid (αABA), which is an intermediate in the biosynthetic pathway of ophthalmic acid.

Therefore, a byproduct amino acid of L-isoleucine may be, but is not limited to, L-valine, L-leucine, L-norvaline, L-norleucine, alpha-aminobutyric acid (αABA) or a combination thereof, in a method for producing L-isoleucine by fermentation of a bacterium belonging to the family Enterobacteriaceae and modified to overexpress the cycA gene, as described hereinafter.

The bacteria belonging to the family Enterobacteriaceae can be from the genera *Enterobacter, Enwinia, Escherichia, Klebsiella, Morganella, Pantoea, Photorhabdus, Providencia, Salmonella, Yersinia*, and so forth, and can have the ability to produce L-isoleucine. Specifically, those classified into the family Enterobacteriaceae according to the taxonomy used in the NCBI (National Center for Biotechnology Information) database (www.ncbi.nlm.nih.gov/Taxonomy/Browser/wwwtax.cgi?id=543) can be used. Examples of bacteria from the family Enterobacteriaceae which can be modified include a bacterium of the genus *Escherichia, Enterobacter* or *Pantoea*.

*Escherichia* bacteria which can be modified to obtain *Escherichia* bacteria in accordance with the presently disclosed subject matter are not particularly limited, and specifically, those described in the work of Neidhardt et al. can be used (Bachmann, B. J., Derivations and genotypes of some mutant derivatives of *E. coli* K-12, p. 2460-2488. In F. C. Neidhardt et al. (ed.), *E. coli* and *Salmonella*: cellular and molecular biology, 2$^{nd}$ ed. ASM Press, Washington, D.C., 1996). The species *E. coli* is a particular example. Specific examples of *E. coli* include *E. coli* W3110 (ATCC 27325), *E. coli* MG1655 (ATCC 47076), and so forth, which are derived from the prototype wild-type strain, *E. coli* K-12 strain. These strains are available from, for example, the American Type Culture Collection (P.O. Box 1549, Manassas, Va. 20108, United States of America). That is, registration numbers are given to each of the strains, and the strains can be ordered by using these registration numbers (refer to www.atcc.org). The registration numbers of the strains are listed in the catalogue of the American Type Culture Collection.

Examples of the *Enterobacter* bacteria include *Enterobacter agglomerans, Enterobacter aerogenes*, and so forth. Examples of the *Pantoea* bacteria include *Pantoea ananatis* (*P. ananatis*), and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. When a *Pantoea ananatis* strain is bred by genetic engineering techniques, *Pantoea ananatis* AJ13355 strain (FERM BP-6614), AJ13356 strain (FERM BP-6615), AJ13601 strain (FERM BP-7207) and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequencing of 16S rRNA and so forth as described above.

L-Isoleucine-Producing Bacteria

Examples of L-isoleucine-producing bacteria or parental strains which can be used to derive L-isoleucine-producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as L-isoleucine-producing bacteria or parental strains thereof (JP 2-458 A, EP0356739 A1, and U.S. Pat. No. 5,998,178). Example of L-isoleucine-producing bacteria or parental strains thereof also includes *E. coli* K-12 strain 44-3-15 Scr (VKPM B-12149).

The bacterium of the present invention belonging to the family Enterobacteriaceae has been modified to overexpress the cycA gene.

The cycA gene (synonyms: dagA, ECK4204, JW4166, ytfD) of *E. coli* encodes the D-alanine/D-serine/glycine transporter CycA (KEGG, Kyoto Encyclopedia of Genes and Genomes, entry No. b4208; Protein Knowledgebase, UniProtKB/Swiss-Prot, accession No. P0AAE0). The cycA gene (GenBank, accession No. NC_000913.3; nucleotide positions: 4429864 to 4431276; Gene ID: 948725) is located between the fklB gene on the same strand and the ytfE gene on the opposite strand on the chromosome of *E. coli* strain K-12. The nucleotide sequence of the cycA gene of *E. coli* strain K-12 (SEQ ID NO: 1) and the amino acid sequence of the CycA protein of *E. coli* strain K-12 (SEQ ID NO: 2) encoded by the cycA gene are known. That is, the cycA gene may have the nucleotide sequence of SEQ ID NO: 1, and the CycA protein may have the amino acid sequence of SEQ ID NO: 2. The phrase "a gene or protein has a nucleotide or amino acid sequence" encompasses cases where a gene or protein comprises the nucleotide or amino acid sequence, and cases where a gene or protein consists of the nucleotide or amino acid sequence.

The CycA protein encoded by the cycA gene is a member of the amino acid-polyamine-organocation (APC) superfamily of amino acid transporters (AAT) (transporter classification (TC) number 2.A.3.1). It is suggested that CycA functions as a proton/serine (or alanine, or glycine) symporter. The CycA transporter is involved in the uptake of glycine, serine and alanine (Robbins J. C. and Oxender D. L. Transport systems for alanine, serine, and glycine in *Escherichia coli* K-12, *J. Bacteriol.*, 1973, 116(1):12-18; Lee M. et al., Transport properties of merodiploids covering the dagA locus in *Escherichia coli* K-12, *J. Bacteriol.*, 1975, 122(3):1001-1005). The transport activity of CycA towards cycloserine was also found (Wargel R. J. et al., Mechanism of D-cycloserine action: transport systems for D-alanine, D-cycloserine, L-alanine, and glycine, *J. Bacteriol.*, 1970, 103(3):778-788). No transport activity was found for L-leucine and L-proline (Lee M. et al., 1975). The homologues of CycA from different bacteria of the family Enterobacteriaceae are known, examples of which are described hereinafter.

The phrase "a bacterium modified to overexpress the cycA gene" can mean that the bacterium has been modified in such a way that in the modified bacterium the total activity of the cycA gene product such as CycA protein is increased as compared with, or the expression level of the cycA gene is higher than that level in, a non-modified strain, for example, a wild-type or parental strain as described above and hereinafter. Examples of a non-modified strain serving as a reference for the above comparison can include a wild-type strain of a microorganism belonging to the genus *Escherichia* such as the *E. coli* MG1655 strain (ATCC 47076), W3110 strain (ATCC 27325), or a microorganism belonging to the genus *Pantoea* such as the *P. ananatis* AJ13355 strain (FERM BP-6614), and so forth.

The phrase "the cycA gene is overexpressed" can mean that the total activity of the cycA gene product such as the CycA protein is increased as compared with a non-modified strain. The total activity of the cycA gene product such as the CycA protein is increased by, for example, increasing the expression level of the cycA gene as compared with a non-modified strain as described hereinafter, or increasing the activity per molecule (may be referred to as a specific activity) of the protein encoded by the cycA gene as compared with a wild-type protein. The bacterium can be modified so that the activity of the CycA protein per cell is increased to 150% or more, 200% or more, 300% or more, of the activity of a non-modified strain.

The phrase "activity of a transporter" can mean the activity of transporting an amino acid, such as, for example, an achiral amino acid and/or an L-amino acid and/or a D-amino acid, such as glycine, D-alanine, L-alanine, and D-serine, which can be transported in a bacterium belonging to the family Enterobacteriaceae. The phrase "activity of a transporter" can also mean the activity of transporting an amino acid, which can be transported in a bacterium belonging to the family Enterobacteriaceae, utilizing the protein having an activity of a transporter having the amino acid sequence of SEQ ID NO: 2.

The phrase "activity of a transporter having the amino acid sequence of SEQ ID NO: 2" can mean the activity of a protein having the amino acid sequence of SEQ ID NO: 2 of transporting an amino acid, which can be transported utilizing the protein having the amino acid sequence of SEQ ID NO: 2 in a bacterium belonging to the family Enterobacteriaceae. It is also acceptable that the phrase "activity of a transporter having the amino acid sequence of SEQ ID NO: 2" can mean the activity of the CycA protein having the amino acid sequence of SEQ ID NO: 2 of transporting the amino acid, which can be transported utilizing the CycA protein in a bacterium belonging to the family Enterobacteriaceae. Specifically, the phrases "activity of a transporter" and "activity of a transporter having the amino acid sequence of SEQ ID NO: 2" can mean the activity of the CycA protein having the amino acid sequence of SEQ ID NO: 2 of transporting an amino acid in the bacterium belonging to the family Enterobacteriaceae, such as, for example, glycine, D-alanine, L-alanine or D-serine, and so forth, or their combination, as long as said one or more amino acids can be transported utilizing the CycA in the bacterium.

The activity of a transporter can be determined by evaluating the transporter activity of CycA. The activity of a transporter can also be determined as a specific activity of the protein per unit weight such as mg or µg. For example, a radioactive labeled amino acid such as, for example, [2-$^{14}$C]glycine can be used to measure uptake of the amino acid (Lee M. et al., 1975; Ghrist A. C. and Stauffer G. V. The *Escherichia coli* glycine transport system and its role in the regulation of the *glycine* cleavage enzyme system, *Microbiol.*, 1995, 141(Pt 1):133-140). The protein concentration can be determined by the Bradford protein assay using bovine serum albumin as a standard (Bradford M. M., *Anal. Biochem.*, 1976, 72:248-254).

The phrase "the cycA gene is overexpressed" can also mean that the expression level of the cycA gene is higher than that level in a non-modified strain. Therefore, the phrase "the cycA gene is overexpressed" can be equivalent to the phrase "expression of the cycA gene is enhanced". The bacterium can be modified so that the expression amount of the cycA gene per cell is increased to 150% or more, 200% or more, 300% or more, of the expression amount of a non-modified strain.

Methods which can be used to enhance expression of the cycA gene include, but are not limited to, increasing the cycA gene copy number, such as the cycA gene copy number in the chromosome of the bacterium and/or in the autonomously replicating plasmid harbored by the bacterium. The cycA gene copy number can be increased by, for example, introducing the cycA gene into the chromosome of the bacterium and/or introducing an autonomously replicating vector containing the cycA gene into the bacterium.

Examples of the vectors include, but are not limited to, broad-host-range plasmids such as pMW118/119, pBR322, pUC19, and the like. The cycA gene can also be introduced into the chromosomal DNA of a bacterium by, for example, homologous recombination, Mu-driven integration, or the like. Only one copy, or two or more copies of the cycA gene may be introduced. For example, homologous recombination can be carried out using sequence with multiple copies in the chromosomal DNA to introduce multiple copies of the cycA gene into the chromosomal DNA. Sequences with multiple copies in the chromosomal DNA include, but are not limited to, repetitive DNA or inverted repeats present at the end of a transposable element. In addition, it is possible to incorporate the cycA gene into a transposon and allow it to be transferred to introduce multiple copies of the cycA gene into the chromosomal DNA. By using Mu-driven integration, more than 3 copies of the gene can be introduced into the chromosomal DNA during a single act (Akhverdyan V. Z. et al., *Biotechnol. (Russian)*, 2007, 3:3-20).

Additional methods which can be used to enhance expression of the cycA gene include increasing the expression level of the cycA gene by modification of expression regulatory region(s) of the cycA gene. Expression regulatory region(s) of the cycA gene can be modified by, for example, replacing the native expression regulatory region(s) of cycA gene with native and/or modified foreign expression regulatory region(s). Expression regulatory region(s) can also be referred to as Expression regulatory sequence(s). Expression regulatory regions can be exemplified by promoters, enhancers, attenuators and termination signals, anti-termination signals, ribosome-binding sites (RBS) and other expression control elements (e.g., regions to which repressors or inducers bind and/or binding sites for transcriptional and translational regulatory proteins, for example, in the transcribed mRNA). Such regulatory regions are described, for example, in Sambrook J., Fritsch E. F. and Maniatis T., "Molecular Cloning: A Laboratory Manual", $2^{nd}$ ed., Cold Spring Harbor Laboratory Press (1989). Modifications of regions controlling gene(s) expression can be combined with increasing the copy number of the gene(s) (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters suitable for enhancing the cycA gene expression can be the potent promoters that are stronger than the native cycA promoter. For example, the lac promoter, the trp promoter, the trc promoter, the tac promoter, the $P_R$ or the $P_L$ promoters of lambda phage are all known to be potent promoters. Potent promoters providing a high level of gene expression in a bacterium belonging to the family Enterobacteriaceae can be used. Alternatively, the effect of a promoter can be enhanced by, for example, introducing a mutation into the promoter region of the cycA gene to obtain a stronger promoter function, thus resulting in the increased transcription level of the cycA gene located downstream of the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1, 1984, 3:623-629).

The copy number, presence or absence of the gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations and the like may be ordinary methods well-known to the person skilled in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

There may be some differences in DNA sequences between the genera, species or strains of the family Enterobacteriaceae. Therefore, the cycA gene is not limited to the gene shown in SEQ ID NO: 1, but may include genes which are variant nucleotide sequences of or homologous to SEQ ID NO: 1, and which encode the CycA protein.

The phrase "a variant protein" can mean a protein which has one or more mutations in the sequence compared with the amino acid sequence of SEQ ID NO: 2, whether they are substitutions, deletions, insertions, and/or additions of one or several amino acid residues, but which still maintains an activity or function similar to that of the CycA protein, such as the activity of a transporter as described above, or of which the three-dimensional structure is not significantly changed relative to the wild-type protein. The number of changes in the variant protein depends on the position in the three-dimensional structure of the protein or the type of amino acid residues. It can be, but is not strictly limited to, 1 to 50, in another example 1 to 30, in another example 1 to 15, in another example 1 to 10, and in another example 1 to 5, in SEQ ID NO: 2. This is because some amino acids have high homology to one another, so that the activity or function of a protein is not affected by a change between such amino acids, or the three-dimensional structure of a protein is not significantly changed relative to the wild-type protein by a change between such amino acids. Therefore, the variant proteins encoded by the cycA gene may have a homology, defined as the parameter "identity" when using the computer program BLAST, of not less than 70%, not less than 75%, not less than 80%, not less than 85%, not less than 90%, not less than 95%, not less than 98%, or not less than 99% with respect to the entire amino acid sequence shown in SEQ ID NO: 2, as long as the activity or function of the CycA protein is maintained, or the three-dimensional structure of CycA protein is not significantly changed relative to the wild-type CycA protein.

The exemplary substitution, deletion, insertion, and/or addition of one or several amino acid residues can be a conservative mutation(s). The representative conservative mutation is a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that the activity or function similar to that of the CycA protein, such as the activity of a transporter as described above, is maintained, or the three-dimensional structure of CycA protein is not significantly changed relative to the wild-type CycA protein.

To evaluate the degree of protein or DNA homology, several calculation methods can be used, such as BLAST search, FASTA search and ClustalW method. The BLAST (Basic Local Alignment Search Tool, www.ncbi.nlm.nih.gov/BLAST/) search is the heuristic search algorithm employed by the programs blastp, blastn, blastx, megablast, tblastn, and tblastx; these programs ascribe significance to their findings using the statistical methods of Karlin S. and Altschul S. F. ("Methods for assessing the statistical significance of molecular sequence features by using general scoring schemes" *Proc. Natl. Acad. Sci. USA*, 1990, 87:2264-2268; "Applications and statistics for multiple high-scoring segments in molecular sequences". *Proc. Natl. Acad. Sci. USA*, 1993, 90:5873-5877). The computer program BLAST calculates three parameters: score, identity and similarity. The FASTA search method is described by Pearson W. R. ("Rapid and sensitive sequence comparison with FASTP and FASTA", *Methods Enzymol.*, 1990, 183: 63-98). The ClustalW method is described by Thompson J. D. et al. ("CLUSTAL W: improving the sensitivity of progressive multiple sequence alignment through sequence weighting, position-specific gap penalties and weight matrix choice", *Nucleic Acids Res.*, 1994, 22:4673-4680).

Protein homologues of CycA (CycA homologues) can also be used as the CycA protein. Examples of CycA homologues include CycA homologues of various organisms such as bacteria of the family Enterobacteriaceae. For example, the CycA homologues from different bacteria of the family Enterobacteriaceae are known, that have the activity of a transporter as described above. Examples of such CycA homologues of the family Enterobacteriaceae are described hereinafter (Table 1) with indication of a homology value (as "identity", that is the identity of amino acids), taxonomy data, and accession and sequence record numbers of amino acid sequences in the NCBI database (National Center for Biotechnology Information, www.ncbi.nlm.nih.gov/protein/). Furthermore, variant proteins of such CycA homologues can also be used as the CycA protein. The aforementioned descriptions concerning variant proteins of the CycA protein of SEQ ID NO: 2, e.g. those regarding mutations and sequence identity, can be applied mutatis mutandis to variant proteins of CycA homologues.

The phrase "the CycA" or "the CycA protein" is not limited to the wild-type CycA proteins such as the CycA protein of SEQ ID NO: 2 and CycA homologues of Table 1, but can correctively refer to the wild-type CycA proteins and variant proteins thereof.

TABLE 1

| Identity | Organism | Accession No.*; Sequence record (GI) No.* |
|---|---|---|
| 100% | *Escherichia coli* (strain K-12) | YP_492350.1; 388480155 |
| 93% | *Klebsiella pneumoniae* | WP_015959296.1; 506439579 |
| 100% | *Shigella sonnei* (strain Ss046) | Q3YUD9; 123615489 |
| 95% | *Salmonella enterica* | WP_000228328.1; 446150473 |
| 94% | *Enterobacter aerogenes* | WP_015368603.1; 505181501 |
| 95% | *Citrobacter freundii* MGH 56 | KDF09506.1; 635727731 |
| 74% | *Pantoea ananatis* | WP_013025298.1; 502790322 |
| 100% | *Klebsiella pneumoniae* IS22 | CDK72727.1; 571213503 |
| 76% | *Pantoea* sp. At-9b | WP_013508580.1; 503273919 |
| 96% | *Enterobacter cloacae* | WP_014168338.1; 503934344 |
| 74% | *Erwinia amylovora* ATCC BAA-2158 | CBX80271.1; 312172014 |
| 100% | *Escherichia coli* O145:H28 (strain RM13516) | AHG17723.1; 573937918 |
| 77% | *Dickeya dadantii* | WP_013318563.1; 503083691 |
| 99% | *Shigella flexneri* | WP_000228331.1; 446150476 |
| 69% | *Morganella morganii* | WP_024473835.1; 639125696 |
| 86% | *Serratia marcescens* | WP_019456240.1; 518286032 |

*in the NCBI database (National Center for Biotechnology Information, www.ncbi.nlm.nih.gov/)

The cycA gene can be any gene encoding CycA protein. For example, the cycA gene can be a variant nucleotide sequence. The phrase "a variant nucleotide sequence" can mean a nucleotide sequence which encodes a variant protein as described above, or a nucleotide sequence which encodes any wild-type CycA protein using any synonymous amino acid codons according to the standard genetic code table (see, e.g., Lewin B., "Genes VIII", 2004, Pearson Education, Inc., Upper Saddle River, N.J. 07458). Therefore, the cycA gene can be a variant nucleotide sequence due to the degeneracy of the genetic code, such as a variant nucleotide sequence of SEQ ID NO: 1 due to the degeneracy of the genetic code.

The phrase "a variant nucleotide sequence" can also mean, but is not limited to, a nucleotide sequence which hybridizes under stringent conditions with the nucleotide sequence complementary to the sequence shown in SEQ ID NO: 1, or a probe which can be prepared from the nucleotide sequence under stringent conditions provided that it encodes active or functional protein. "Stringent conditions" include those under which a specific hybrid, for example, a hybrid having homology, defined as the parameter "identity" when using the computer program BLAST, of not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate), or in another example, 0.1×SSC, 0.1% SDS at 60° C. or 65° C.

Duration of washing depends on the type of membrane used for blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR using oligonucleotides as primers prepared on the basis of the sequence shown in SEQ ID NO: 1 and a DNA fragment containing the nucleotide sequence as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after hybridization can be exemplified by 2×SSC, 0.1% SDS at 50° C., 60° C. or 65° C.

As the gene encoding the CycA protein of the species *E. coli* has already been elucidated (see above), the cycA gene, such as genes encoding the wild-type CycA proteins or variant proteins thereof, can be obtained by PCR (polymerase chain reaction; refer to White T. J. et al., The polymerase chain reaction, *Trends Genet.,* 1989, 5:185-189) from a microorganism harboring a wild-type cycA gene, for example, a bacterium belonging to the family Enterobacteriaceae, utilizing primers prepared based on the nucleotide sequence of the cycA gene; or the site-directed mutagenesis method by treating a DNA containing the wild-type cycA gene in vitro, for example, with hydroxylamine, or a method for treating a microorganism harboring a wild-type cycA gene, for example, a bacterium belonging to the family Enterobacteriaceae, with ultraviolet (UV) irradiation or a mutating agent such as N-methyl-N'-nitro-N-nitrosoguanidine (NTG) and nitrous acid usually used for the such treatment; or chemically synthesized as full-length gene structure. Thus, genes encoding the wild-type CycA proteins such as the CycA protein of *E. coli* and CycA protein homologues of other microorganisms of the family Enterobacteriaceae or genes encoding variant proteins thereof can be obtained.

The phrase "the cycA gene" is not limited to the wild-type cycA genes such as the cycA gene of SEQ ID NO: 1 and genes encoding CycA homologues of Table 1, but can correctively refer to the native cycA genes and genes encoding variant CycA proteins.

The phrase "a wild-type protein" can mean a native protein naturally produced by a wild-type or parent bacterial strain of the family Enterobacteriaceae, for example, by the wild-type *E. coli* MG1655 strain. A wild-type protein can be encoded by the "wild-type gene", which can be present in genome of a wild-type bacterium.

The above descriptions concerning variants of the genes and proteins can also be applied mutatis mutandis to arbitrary proteins such as L-isoleucine biosynthesis enzymes and genes coding for them.

The bacterium can have, in addition to the properties already mentioned, other specific properties such as various nutrient requirements, drug resistance, drug sensitivity, and drug dependence, without departing from the scope of the present invention.

2. Method

A method of the present invention includes the method for producing L-isoleucine. The method for producing L-isoleucine can include the steps of cultivating the bacterium in a culture medium to allow L-isoleucine to be produced, excreted or secreted, and/or accumulated in the culture medium or in the bacterial cells, or both, and collecting L-isoleucine from the culture medium and/or the bacterial cells. L-isoleucine can be produced in a free form or as a salt thereof, or as a mixture thereof. That is, the phrase "L-isoleucine" may refer to L-isoleucine in a free form, a salt thereof, or a mixture thereof. For example, sodium, potassium, ammonium, and the like salts or an inner salt such as zwitterion of L-isoleucine can be produced by the method. This is possible as amino acids can react under fermentation conditions with each other or a neutralizing agent such as an inorganic or organic acidic or alkaline substance in a typical acid-base neutralization reaction to form a salt that is the chemical feature of amino acids which is apparent to one skilled in the art.

Moreover, the method of the present invention for producing L-isoleucine further includes a method for reducing production of byproduct amino acid(s) of L-isoleucine. The method for reducing production of byproduct amino acid(s) of L-isoleucine can include the steps of cultivating the bacterium in a culture medium to allow L-isoleucine to be produced, excreted or secreted, and/or accumulated in the culture medium or in the bacterial cells, or both, collecting and, if necessary, purifying L-isoleucine from the culture medium and/or the bacterial cells.

The cultivation of the bacterium, and collection and purification of L-isoleucine from the medium and the like may be performed in a manner similar to conventional fermentation methods wherein L-isoleucine is produced using a microorganism. The culture medium for production of the L-isoleucine can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolyzates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B 1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under aerobic conditions for 16 to 72 h, or for 32 to 68 h; the culture temperature during cultivation can be controlled within 30 to 45° C., or within 30 to 37° C.; and the pH can be adjusted between 5 and 8, or between 6 and 7.5. The pH can be adjusted by using an inorganic or organic acidic or alkaline substance, as well as ammonia gas.

After cultivation, L-isoleucine can be collected from the culture medium. Also, after cultivation, the cells can be disrupted with, for example, supersonic waves or the like, the supernatant can be obtained by removing solids such as the cells and the cell-disrupted suspension (also referred to as cell debris) by, for example, centrifugation or membrane filtration, and then L-isoleucine can be collected from the supernatant. Collection of L-isoleucine from the culture medium or the supernatant etc can be performed by any combination of conventional techniques such as concentration, ion-exchange chromatography, and crystallization.

The collected L-isoleucine may contain, for example, microbial cells, medium components, moisture, by-product metabolites of the microorganism, and so forth, in addition to L-isoleucine. Purity of the collected L-isoleucine can be 50% or higher, 85% or higher, or 95% or higher (U.S. Pat. No. 5,431,933, Japanese Patent No. 1214636, U.S. Pat. Nos. 4,956,471, 4,777,051, 4,946,654, 5,840,358, 6,238,714, U.S. Patent Published Application No. 2005/0025878).

EXAMPLES

The present invention will be more specifically explained below with reference to the following non-limiting examples.

Example 1. Construction of the *E. coli* L-Isoleucine-Producing Strain Modified to Overexpress the cycA Gene 1.1 Construction of the *E. coli* MG1655 Strain Having Modified a Regulatory Region of cycA The cycA gene in *E. coli* was overexpressed using the method developed by Datsenko K. A. and Wanner B. L. called "λRed/ET-mediated integration" (Datsenko K. A. and Wanner B. L., *Proc. Natl. Acad. Sci. USA*, 2000, 97(12): 6640-6645). According to this procedure, the PCR primers P1 (SEQ ID NO: 3) and P2 (SEQ ID NO: 4), which are homologous to both regions adjacent to the cycA gene and regions adjacent to the cat gene conferring chloramphenicol resistance ($Cm^R$) and the $P_L$ promoter in the template chromosome, were constructed. The chromosome of the chloramphenicol-resistant *E. coli* strain BW25113 cat-$P_L$-yddG, which contains the early $P_L$ promoter region of phage lambda (Giladi H. et al., Identification of an UP element within the IHF binding site at the PL1-PL2 tandem promoter of bacteriophage lambda, *J. Mol. Biol.*, 1996, 260(4):484-491), was used as the template in PCR reaction. The *E. coli* strain BW25113 cat-$P_L$-yddG can be constructed as described in detail in EP1449918 A1. The *E. coli* strain BW25113 can be obtained from the Coli Genetic Stock Center (Yale University, New Haven, USA) as CGSC7636.

Conditions for PCR were as follows: denaturation for 3 min at 95° C.; profile for 35 cycles: 1 min at 95° C., 1 min at 58° C., 1 min at 72° C.; final elongation for 5 min at 72° C. The obtained DNA-fragment 1 (1,964 bp) (SEQ ID NO: 5) was purified in an agarose gel and used for electroporation of the strain *E. coli* MG1655 (ATCC 47076) containing the plasmid pKD46 with a temperature-sensitive replication origin. *E. coli* MG1655 is available from the American Type Culture Collection (P.O. Box 1549, Manassas, Va. 20108, United States of America). The plasmid pKD46 (Datsenko K. A. and Wanner B. L., *Proc. Natl. Acad. Sci. USA*, 2000, 97(12):6640-6645) includes a 2,154 nt (31088-33241) DNA-fragment of phage λ (GenBank, accession No. J02459) and contains genes of the λRed homologous recombination system (γ, β, and exo genes) under the control of arabinose-inducible $P_{araB}$ promoter. The plasmid pKD46 is necessary to integrate the DNA-fragment into the chromosome of strain *E. coli* MG1655.

Electrocompetent cells were prepared as follows: *E. coli* MG1655 cells were grown overnight at 30° C. in LB-medium (Sambrook, J. and Russell, D. W. "Molecular Cloning: A Laboratory Manual", $3^{rd}$ ed., Cold Spring Harbor Laboratory Press (2001)) containing ampicillin (100 mg/L), and the culture was diluted 100 times with 5 mL of SOB-medium (Sambrook J., Fritsch E. F. and Maniatis T., "Molecular Cloning: A Laboratory Manual", $2^{nd}$ ed., Cold Spring Harbor Laboratory Press (1989)) containing ampicillin (100 mg/L) and L-arabinose (1 mM). The diluted culture was grown with aeration (250 rpm) at 30° C. to an $OD_{600}$ of about 0.6 and then made electrocompetent by concentrating 100-fold and washing three times with ice-cold deionized $H_2O$. Electroporation was performed using 70 μL of cells and about 100 ng of the DNA-fragment 1. Then, cells were incubated with 1 mL of SOC-medium (Sambrook J., Fritsch E. F. and Maniatis T., "Molecular Cloning: A Laboratory Manual", $2^{nd}$ ed., Cold Spring Harbor Laboratory Press (1989)) at 37° C. for 2.5 h, placed onto the plates containing LB-medium (Sambrook, J. and Russell, D. W. "Molecular Cloning: A Laboratory Manual", $3^{rd}$ ed., Cold Spring Harbor Laboratory Press (2001)), agar (1.5%) and chloramphenicol (20 mg/L), and grown at 37° C. to select $Cm^R$-recombinants. To eliminate the pKD46 plasmid, 1 passage on L-agar with chloramphenicol (20 mg/L) at 42° C. was performed, and the obtained colonies were tested for sensitivity to ampicillin. Thus the strain *E. coli* MG1655 cat-$P_L$-cycA was obtained.

1.2. Verification of a Modification of the Regulatory Region of cycA Gene

Cells containing a heterologous promoter region of the cycA gene marked with $Cm^R$-gene (cat) were verified by PCR using locus-specific primers P3 (SEQ ID NO: 6) and P4 (SEQ ID NO: 7). Conditions for PCR were as follows: denaturation for 3 min at 95° C.; profile for 20 cycles: 30 sec at 95° C., 30 sec at 60° C., 2 min at 72° C.; final elongation for 5 min at 72° C. DNA-fragment 2, obtained in the reaction with the chromosomal DNA from the parent strain *E. coli* MG1655 as the template, was 457 bp in length (SEQ ID NO: 8). DNA-fragment 3, obtained in the reaction with chromosomal DNA from the strain *E. coli* MG1655 cat-$P_L$-cycA as a template, was 2,174 bp in length (SEQ ID NO: 9).

1.3. Construction of the *E. coli* L-Isoleucine-Producing Strain

The cycA gene under control of $P_L$ promoter was introduced into the L-isoleucine-producing *E. coli* K-12 strain 44-3-15 Scr (U.S. Pat. Nos. 6,960,455 B2 and 7,179,623 B2; Russian Patent No. 2212447 C2). The *E. coli* K-12 strain 44-3-15 Scr (also referred to as *E. coli* 44-3-15 Scr) was deposited in the Russian National Collection of Industrial Microorganisms (VKPM, Russian Federation, 117545 Moscow, $1^{st}$ Dorozhny Proezd, 1) on Dec. 17, 2014 according to the provisions of the Budapest Treaty under the accession number of VKPM B-12149. The *E. coli* 44-3-15 Scr has a mutation in the ilvG gene ($ilvG_5$) that results in restoration of acetohydroxy acid synthase II activity, a mutation in the ilvA gene ($ilvA_{7434}$) that results in threonine deaminase insensitivity to feedback inhibition by isoleucine (Gavrilova et al., *Biotechnologiya* (in Russian), 1988, 4:600-608), and is resistant to chloramphenicol ($Cm^R$). Before introduction into the *E. coli* 44-3-15 Scr, the $Cm^R$-marker upstream of the $P_L$ promoter in the expression cassette cat-$P_L$-cycA was replaced with the kanamycin resistance ($Km^R$) marker using λRed integration (Datsenko K. A. and Wanner B. L., *Proc. Natl. Acad. Sci. USA,* 2000, 97(12):6640-6645). According to this procedure, the PCR primers P5 (SEQ ID NO: 10) and P6 (SEQ ID NO: 11), which are homologous to both regions adjacent to the cat gene and the kan gene conferring kanamycin resistance ($Km^R$) in the template plasmid, were constructed. The plasmid pMW118-(λattL-$Km^R$-λattR) was used as the template in the PCR reaction (EP2100957 A1).

Conditions for PCR were as follows: denaturation for 3 min at 95° C.; profile for 35 cycles: 30 sec at 94° C., 30 sec at 57° C., 1 min 30 sec at 72° C.; final elongation for 5 min at 72° C. The obtained DNA-fragment 4 (1,541 bp) (SEQ ID NO: 12) was purified in an agarose gel and used for electroporation of the strain *E. coli* MG1655 cat-$P_L$-cycA (Example 1.1) containing the plasmid pKD46 (Datsenko K. A. and Wanner B. L., *Proc. Natl. Acad. Sci. USA,* 2000, 97(12):6640-6645). The cells of *E. coli* MG1655 strain, that harbor the kan-$P_L$-cycA cassette, were selected on the plates containing LB-medium, agar (1.5%) and kanamycin (40 mg/L). Thus, the kanamycin-resistant chloramphenicol-sensitive strain *E. coli* MG1655 kan-$P_L$-cycA was obtained.

The replacement of the $Cm^R$-marker upstream of the $P_L$-cycA construct was verified by PCR. For this purpose, the primers P3 (SEQ ID NO: 6) and P4 (SEQ ID NO: 7) were used. Conditions for PCR were as follows: denaturation for 3 min at 95° C.; profile for 20 cycles: 30 sec at 95° C., 30 sec at 60° C., 2 min at 72° C.; final elongation for 5 min at 72° C. DNA-fragment 3, obtained in the reaction with the chromosomal DNA from the parent strain *E. coli* MG1655 cat-$P_L$-cycA as the template, was 2,174 bp in length (SEQ ID NO: 9). DNA-fragment 5, obtained in the reaction with the chromosomal DNA from the strain *E. coli* MG1655 kan-$P_L$-cycA as a template, was 2,087 bp in length (SEQ ID NO: 13).

Then, the expression cassette kan-$P_L$-cycA was introduced into the L-isoleucine producing strain *E. coli* 44-3-15 Scr by P1-transduction (Miller J. H. "Experiments in molecular genetics", Cold Spring Harbor Laboratory, Cold Spring Harbor (1972)). Cells of the *E. coli* 44-3-15 Scr strain that harbor the kan-$P_L$-cycA cassette were selected on the plates containing LB-medium, agar (1.5%) and kanamycin (40 mg/L). Thus, the L-isoleucine producing strain *E. coli* 44-3-15 Scr kan-$P_L$-cycA was obtained. The replacement of a promoter region of the cycA gene was verified by PCR as described above.

Example 2. By-Production of L-Valine Using the *E. coli* 44-3-15 Scr Kan-$P_L$-cycA Strain The modified *E. coli* 44-3-15 Scr kan-$P_L$-cycA and the control *E. coli* 44-3-15 Scr strains were each cultivated at 32° C. for 18 hours in LB-medium (also referred to as lysogenic broth or Luria-Bertani medium as described in Sambrook, J. and Russell, D. W. "Molecular Cloning: A Laboratory Manual", 3$^{rd}$ ed., Cold Spring Harbor Laboratory Press (2001)). Then, 0.2 mL of the obtained culture was inoculated into 2 mL of a fermentation medium in 20×200-mm test tubes and cultivated at 32° C. for 66 hours on a rotary shaker at 250 rpm to an $OD_{550}$ of about 29 until glucose was consumed.

The composition of the fermentation medium (g/L) was as follows:

| | |
|---|---|
| Glucose | 60.0 |
| $(NH_4)_2SO_4$ | 15.0 |
| $KH_2PO_4$ | 1.5 |
| $MgSO_4 \cdot 7H_2O$ | 1.0 |
| Thiamine-HCl | 0.1 |
| L-threonine | 4.0 |
| $CaCO_3$ | 25.0 |
| LB-medium | 10% (v/v) |

The fermentation medium was sterilized at 116° C. for 30 min, except that glucose and $CaCO_3$ were sterilized separately as follows: glucose at 110° C. for 30 min and $CaCO_3$ at 116° C. for 30 min. The pH was adjusted to 7.0 by KOH solution.

After cultivation, the accumulated L-isoleucine and L-valine were measured using thin-layer chromatography (TLC). TLC plates (10×20 cm) were coated with 0.11-mm layers of Sorbfil silica gel containing non-fluorescent indicator (Sorbpolymer, Krasnodar, Russian Federation). Samples were applied onto the plates with the Camag Linomat 5 sample applicator. The Sorbfil plates were developed with a mobile phase consisting of propan-2-ol:ethylacetate:25% aqueous ammonia:water (16:16:5:10, v/v). A solution of ninhydrin (2%, w/v) in acetone was used as the visualizing reagent. After development, plates were dried and scanned with the Camag TLC Scanner 3 in absorbance mode with detection at 520 nm using winCATS software (version 1.4.2).

The results of four independent test-tube fermentations are shown in Table 2. The amount of L-valine was determined as a relative value based on the value for L-isoleucine as a control, which was taken as 100%. As it can be seen from the Table 2, the modified *E. coli* 44-3-15 Scr kan-$P_L$-cycA strain was able to accumulate a higher amount of L-isoleucine as compared with the parent *E. coli* 44-3-15 Scr strain. Table 2 also shows that the modified *E. coli* 44-3-15 Scr kan-$P_L$-cycA strain was able to accumulate less L-valine as compared with the parent *E. coli* 44-3-15 Scr strain.

TABLE 2

| Strain | L-Ile, g/L | L-Val, % of L-Ile |
|---|---|---|
| *E. coli* 44-3-15 Scr | 13.7 | 23.5 |
| *E. coli* 44-3-15 Scr kan-$P_L$-cycA | 14.0 | 16.0 |

Example 3. By-Production of Alpha-Aminobutyric Acid and Norvaline Using the *E. coli* 44-3-15 Scr kan-$P_L$-cycA Strain The modified *E. coli* 44-3-15 Scr kan-$P_L$-cycA and the control *E. coli* 44-3-15 Scr strains were each cultivated at 32° C. for 18 hours in LB-medium. Then, 0.2 mL of the obtained culture was inoculated into 2 mL of a fermentation medium in 20×200-mm test tubes and cultivated at 32° C. for 66 hours on a rotary shaker at 250 rpm to an $OD_{550}$ of about 29 until glucose consumption. The fermentation medium was supplemented with chlorsulfuron (CAS number 64902-72-3) to decrease biosynthesis of branched-chain L-amino acids by inhibiting acetolactate synthase (AHAS) to demonstrate the effect from overexpression of cycA on by-production of alpha-aminobutyric acid and norvaline (Gedi V. and Yoon M.-Y., Bacterial acetohydroxyacid synthase and its inhibitors—a summary of their structure, biological activity and current status, *FEBS J.,* 2012, 279 (6):946-963).

The composition of the fermentation medium (g/L) was as follows:

|  |  |
|---|---|
| Glucose | 60.0 |
| $(NH_4)_2SO_4$ | 15.0 |
| $KH_2PO_4$ | 1.5 |
| $MgSO_4 \cdot 7H_2O$ | 1.0 |
| Thiamine-HCl | 0.1 |
| Chlorsulfuron | 20 µM |
| $CaCO_3$ | 25.0 |
| LB-medium | 10% (v/v) |

The fermentation medium was sterilized at 116° C. for 30 min, except that glucose and $CaCO_3$ were sterilized separately as follows: glucose at 110° C. for 30 min and $CaCO_3$ at 116° C. for 30 min. The pH was adjusted to 7.0 by KOH solution.

After cultivation, the accumulated L-isoleucine, alpha-aminobutyric acid and norvaline were measured using high-performance liquid chromatography (HPLC) (Auxiliary example).

The results of three independent test-tube fermentations are shown in Table 3. The amount of alpha-aminobutyric acid (αABA) and norvaline (nVal) was determined as a relative value based on the value for L-isoleucine as a control, which was taken as 100%. As it can be seen from the Table 3, the modified *E. coli* 44-3-15 Scr kan-$P_L$-cycA strain was able to accumulate a lower amount of αABA and nVal as compared with the parent *E. coli* 44-3-15 Scr strain.

TABLE 3

| Strain | L-Ile, mg/L | αABA, % of L-Ile | nVal, % of L-Ile |
|---|---|---|---|
| *E. coli* 44-3-15 Scr | 270 | 274 | 337 |
| *E. coli* 44-3-15 Scr kan-$P_L$-cycA | 113 | <9 | 105 |

Auxiliary Example. Chromatographic Analysis for L-Isoleucine, Alpha-Aminobutyric Acid and Norvaline The Waters AccQ-Tag Method was used for the analysis. The AccQ-Tag Method is a precolumn derivatization technique for determination of amino acids. The HPLC system Agilent 1100 gradient system (Agilent Technologies) equipped with fluorescence detector and connected to computer loaded with "ChemStation B.02.01 SR2" chromatography software (Agilent Technologies) was used. The detector settings were as follows: excitation wavelength at 250 nm, emission wavelength at 395 nm. A 5 µL sample injection loop was used for all runs. Waters AccQ-Tag Amino Acid Analysis Column (3.9×150 mm) equipped with a guard column was used to resolve the amino acid derivatives obtained in the AccQ-Fluor derivatization reaction using the AccQ-Fluor Reagent Kit (Waters, WAT052880). The column was equilibrated at 37° C., and a mobile-phase at a flow-rate of 0.8 mL/min was applied. The mobile phase contained the following eluents: A—aqueous buffer Waters AccQ-Tag Eluent A (Waters, WAT052890), B—HPLC-grade acetonitrile, and C—Milli-Q water. The gradient was as shown in the Table 4. The curve No. 6 corresponds to a linear segment and No. 11 to a step function.

TABLE 4

| Step | Start time of a step, min | Eluent A, % | Eluent B, % | Eluent C, % | Curve type |
|---|---|---|---|---|---|
| 1 | 0 | 100 | 0 | 0 | 0 |
| 2 | 0.4 | 100 | 0 | 0 | 6 |
| 3 | 0.5 | 99 | 1 | 0 | 6 |
| 4 | 18.0 | 95 | 5 | 0 | 6 |
| 5 | 19.0 | 91 | 9 | 0 | 6 |
| 6 | 28.0 | 78 | 17 | 5 | 6 |
| 7 | 35.0 | 78 | 17 | 5 | 11 |
| 8 | 36.0 | 0 | 60 | 40 | 11 |
| 9 | 38.0 | 0 | 60 | 40 | 11 |
| 10 | 39.0 | 100 | 0 | 0 | 11 |
| 11 | 47.0 | 99 | 1 | 0 | 11 |

INDUSTRIAL APPLICABILITY

The method of the present invention is useful for the production of L-isoleucine in a higher amount with the high grade of purity.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

What is claimed is:

1. A method for producing L-isoleucine comprising:
   (i) cultivating an *Escherichia coli* bacterium that produces L-isoleucine in a culture medium or in cells of the bacterium, or both; and
   (ii) collecting the L-isoleucine from the culture medium or the cells, or both,
   wherein the bacterium has been modified to overexpress a cycA gene by increasing the copy number of the cycA gene and/or by modifying an expression regulatory region of the cycA gene, so that the expression of said gene is enhanced as compared with a non-modified bacterium.

2. The method of claim 1, wherein said cycA gene encodes a protein selected from the group consisting of:
   (A) a protein comprising the amino acid sequence of SEQ ID NO: 2;
   (B) a protein comprising the amino acid sequence of SEQ ID NO: 2, having 1 to 10 mutations comprising substitution, deletion, insertion and/or addition of one or several amino acid residues, and wherein said protein has the activity of a transporter having the amino acid sequence of SEQ ID NO: 2; and
(C) a protein having at least 90% homology with the amino acid sequence of SEQ ID NO: 2 and having the activity of a transporter.

3. The method of claim 1, wherein said cycA gene is a DNA selected from the group consisting of:
(A) a DNA comprising the nucleotide sequence of SEQ ID NO: 1;
(B) a DNA encoding a protein comprising the amino acid sequence of SEQ ID NO: 2, having 1 to 10 mutations comprising substitution, deletion, insertion and/or addition of one or several amino acid residues, and wherein said protein has the activity of a transporter; and
(C) a DNA which is a variant nucleotide sequence of SEQ ID NO: 1 due to the degeneracy of the genetic code.

4. The method of claim 1, wherein the *Escherichia coli* bacterium further produces a byproduct amino acid in an amount less than that produced by a non-modified bacterium, wherein the byproduct amino acid is selected from the group consisting of L-valine, L-leucine, L-norvaline, L-norleucine, alpha-aminobutyric acid, and combinations thereof.

* * * * *